United States Patent [19]
Powell et al.

[11] Patent Number: 5,571,481
[45] Date of Patent: Nov. 5, 1996

[54] MAGNETIC CAPTURE RACK WITH SLIDABLE MAGNETIC MEMBER

[75] Inventors: Ralph Powell, Spring, Tex.; Alisa Phillips, Tyngsboro; Barbara Jackson, Watertown, both of Mass.

[73] Assignee: Vicam, L.P., Somerville, Mass.

[21] Appl. No.: 390,784

[22] Filed: Feb. 17, 1995

[51] Int. Cl.$^6$ ............................................. B01L 9/06
[52] U.S. Cl. ..................... 422/104; 209/215; 209/217; 209/636; 210/222; 211/71; 211/74; 422/99; 422/101; 435/288.3; 435/305.1; 435/809; 436/526; 436/809
[58] Field of Search ............................ 422/99, 101, 102, 422/104; 209/636, 212–217, 223.1; 210/695, 222; 435/300, 301, 809; 436/526, 809; 211/60.1, 71, 74

[56] References Cited

U.S. PATENT DOCUMENTS

| | | | |
|---|---|---|---|
| 4,272,510 | 6/1981 | Smith et al. | 427/47 |
| 4,411,868 | 10/1983 | Noack | 422/104 |
| 4,438,068 | 3/1984 | Forrest | 422/61 |
| 4,587,221 | 5/1986 | Cais et al. | 436/500 |
| 4,649,116 | 3/1987 | Daty et al. | 435/287 |
| 4,751,053 | 6/1988 | Dodin et al. | 422/101 |
| 4,895,560 | 1/1990 | Papantonakos | 604/22 |
| 4,895,650 | 1/1990 | Wang et al. | 210/222 |
| 4,910,148 | 3/1990 | Sorensen et al. | 209/213 |
| 4,916,081 | 4/1990 | Kamada et al. | 436/526 |
| 4,988,618 | 1/1991 | Li et al. | 435/6 |
| 5,051,177 | 9/1991 | Dauclez | 210/222 |
| 5,098,663 | 3/1992 | Berthold et al. | 422/104 |
| 5,147,529 | 9/1992 | Lee et al. | 210/695 |
| 5,318,914 | 6/1994 | Matte et al. | 436/526 |

FOREIGN PATENT DOCUMENTS

| | | |
|---|---|---|
| 0136126 | 4/1985 | European Pat. Off. . |
| 0605003 | 7/1994 | European Pat. Off. . |

OTHER PUBLICATIONS

Ithakissios et al., Clin Chem. vol. 23(11) pp. 2072–2079.

Primary Examiner—Jill Warden
Assistant Examiner—Jan M. Ludlow
Attorney, Agent, or Firm—Birch, Stewart, Kolasch & Birch, LLP

[57] ABSTRACT

A magnetic capture rack is disclosed for holding a plurality of tubes, the magnetic capture rack including a primary housing member having a stepped upper surface, a substantially planar base surface, and a longitudinal bore formed in the primary housing. The longitudinal bore is open at least at one end thereof, and a plurality of linearly arranged wells are formed in the stepped upper surface of the housing on opposing sides of the longitudinal bore and along substantially an entire length of the primary housing. A slidable magnetic member is provided which conforms in outer surface shape to an inner surface shape of the longitudinal bore, the magnetic member being selectively slidable into and out of the longitudinal bore.

28 Claims, 3 Drawing Sheets

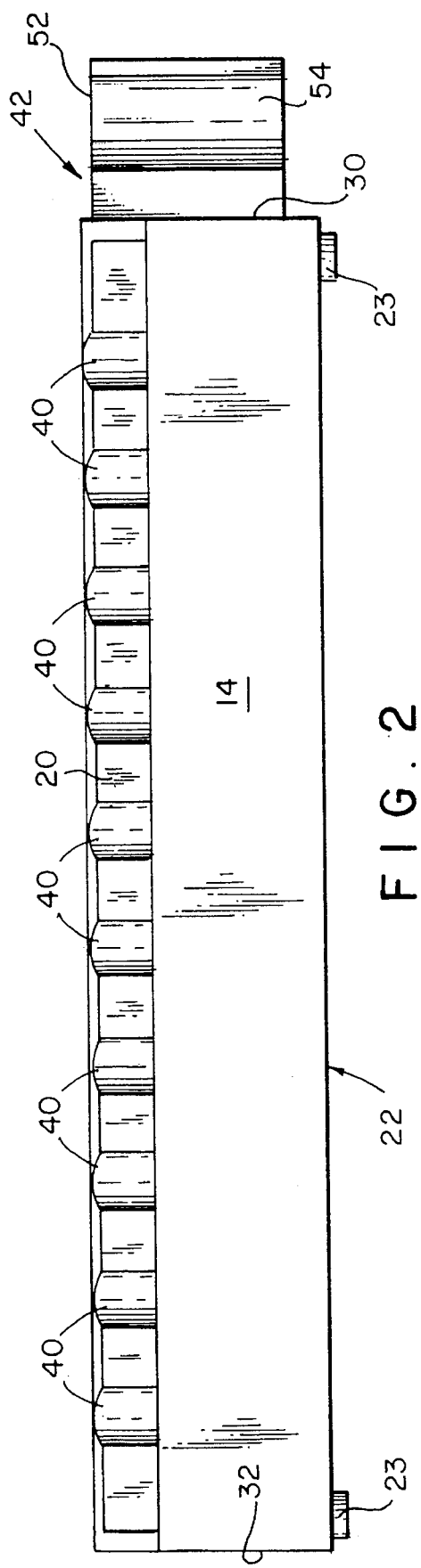
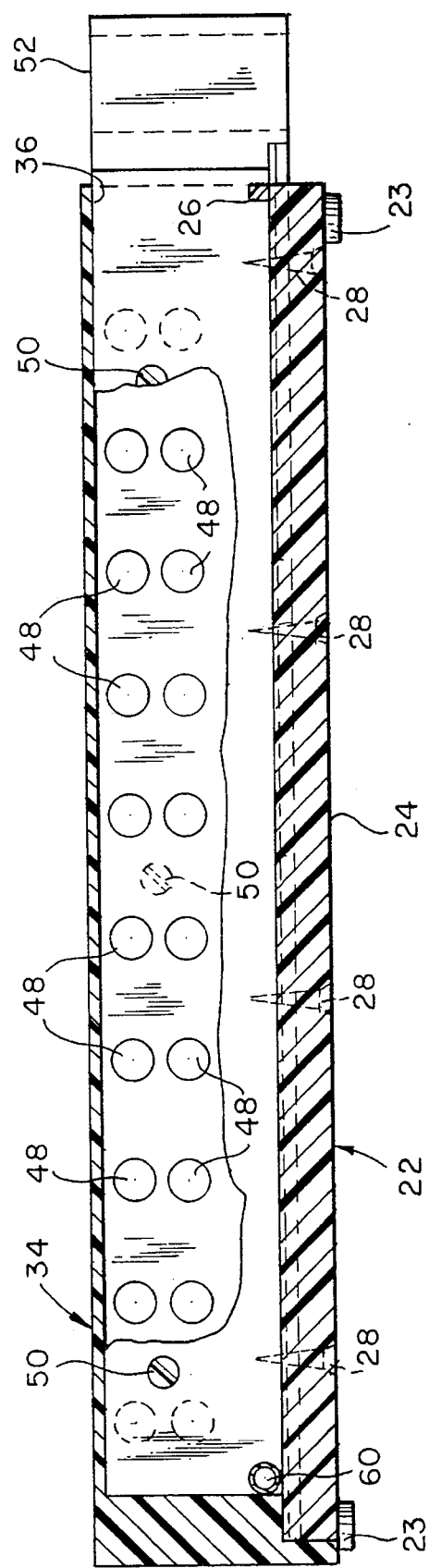
FIG. 2
FIG. 4

MAGNETIC CAPTURE RACK WITH SLIDABLE MAGNETIC MEMBER

BACKGROUND OF THE INVENTION

1. Field of the Invention

The present invention is directed to a magnetic capture rack and, more particularly to a magnetic capture rack having a slidable magnetic member selectively insertable and removable from a housing of the magnetic capture rack.

2. Description of Related Art

Heretofore, magnetic capture racks have been provided in the art for the purpose of removing magnetic particles from suspension in assaying processes.

Usually, assaying takes place with batches of test tubes placed in a rack and a separation step occurs by aligning individual test tubes with the magnets. This step of alignment requires handling of the plurality of test tubes, usually in unison, or handling of the magnets with respect to the test tubes. Movement of the test tubes can be problematic, however, particularly due to the fragile nature of the test tubes. Also, when filled test tubes are moved, splashing of the contents will occur, possibly causing cross-contamination between test tubes, or contamination of an operator. Further, handling of the magnets can reduce the magnetic strength thereof and it is thus the practice in the art to reduce or eliminate the handling of the magnets with respect to the plurality of test tubes. This difficulty in handling either of the test tubes or the magnets poses a problem in the art which is solved by the present invention. The present invention is particularly intended for use in an assaying process such as that disclosed in European Patent No. 0 605 003 A2 published on Jul. 6, 1994 and incorporated herein by reference.

OBJECTS AND SUMMARY OF THE INVENTION

It is an object of the present invention to provide a magnetic capture rack for holding a plurality of test tubes such that the content of the test tubes is easily visible for testing and evaluation of the contents therein.

It is a further object of the present invention to provide a magnetic capture rack in which the plurality of test tubes will remain stationary during testing, while a magnetic member is selectively introduced into and removed from a housing of the magnetic capture rack in a slidable manner.

A still further object of the present invention is to provide the magnetic member with an easily graspable handle portion for movement of the magnetic member, thereby reducing the manual handling of the magnetic member.

These and other objects of the present invention are achieved by providing a magnetic capture rack for holding a plurality of tubes, said rack comprising:

a primary housing member having a stepped upper surface, a substantially planar base surface, and a longitudinal bore formed in said primary housing, wherein the longitudinal bore is open at least at one end thereof;

a plurality of linearly arranged wells formed in the stepped upper surface of said housing on opposing sides of the longitudinal bore and along substantially an entire length of said primary housing;

a slidable magnetic member conforming in outer surface shape to an inner surface shape of the longitudinal bore, said magnetic member being selectively slidable into and out of the longitudinal bore.

The magnetic capture rack includes a plurality of linearly arranged wells evenly spaced in the housing with the linearly arranged wells formed as a single row along opposite sides of the longitudinal bore within the stepped surface of the primary housing member. Further, the slidable magnetic member is substantially equal in length to the primary housing member and is bidirectionally and manually movable in the longitudinal bore. More specifically, the slidable magnetic member includes a pair of elongated non-magnetic bars and an elongated magnetic plate sandwiched between the pair of elongated nonmagnetic bars. An end of the slidable magnetic member includes a gripping portion continually exposed to an exterior of the primary housing member.

The objects of the present invention are also achieved by providing a magnetic capture rack for holding a plurality of tubes, said rack comprising:

a primary housing member having a stepped upper surface, a substantially planar base surface, and a longitudinal bore formed in said primary housing;

means for supporting said plurality of tubes within said primary housing, said means for supporting being formed in the stepped upper surface of said primary housing at a predetermined depth and adjacent at least one side of the longitudinal bore; and a slidable magnetic member conforming in outer surface shape to an inner surface shape of the longitudinal bore, said magnetic member being selectively slidable into and out of the longitudinal bore and adjacent said means for supporting;

wherein a sliding insertion of said magnetic member within said bore attracts magnetic particles in suspension within said plurality of tubes toward said magnetic member and wherein a sliding removal of said magnetic member from said longitudinal bore releases the magnetic particles into suspension within said plurality of tubes.

The means for supporting includes a plurality of evenly spaced wells formed in the housing with the wells formed as a single row each along opposite sides of the longitudinal bore within the stepped surface of the primary housing member. The slidable magnetic member is substantially equal in length to the primary housing member and is bidirectionally and manually movable in the longitudinal bore. Further, the slidable magnetic member includes a pair of elongated non-magnetic bars and an elongated magnetic plate sandwiched between the pair of elongated non-magnetic bars. An end of the slidable magnetic member includes a gripping portion continually exposed to an exterior of the primary housing member.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention and wherein:

FIG. 2 is a longitudinal side view of the rack shown in FIG. 1;

FIG. 4 is a cross-sectional view taken along lines 4—4 of FIG. 1; and

DETAILED DESCRIPTION OF PREFERRED EMBODIMENTS

Figure 1:
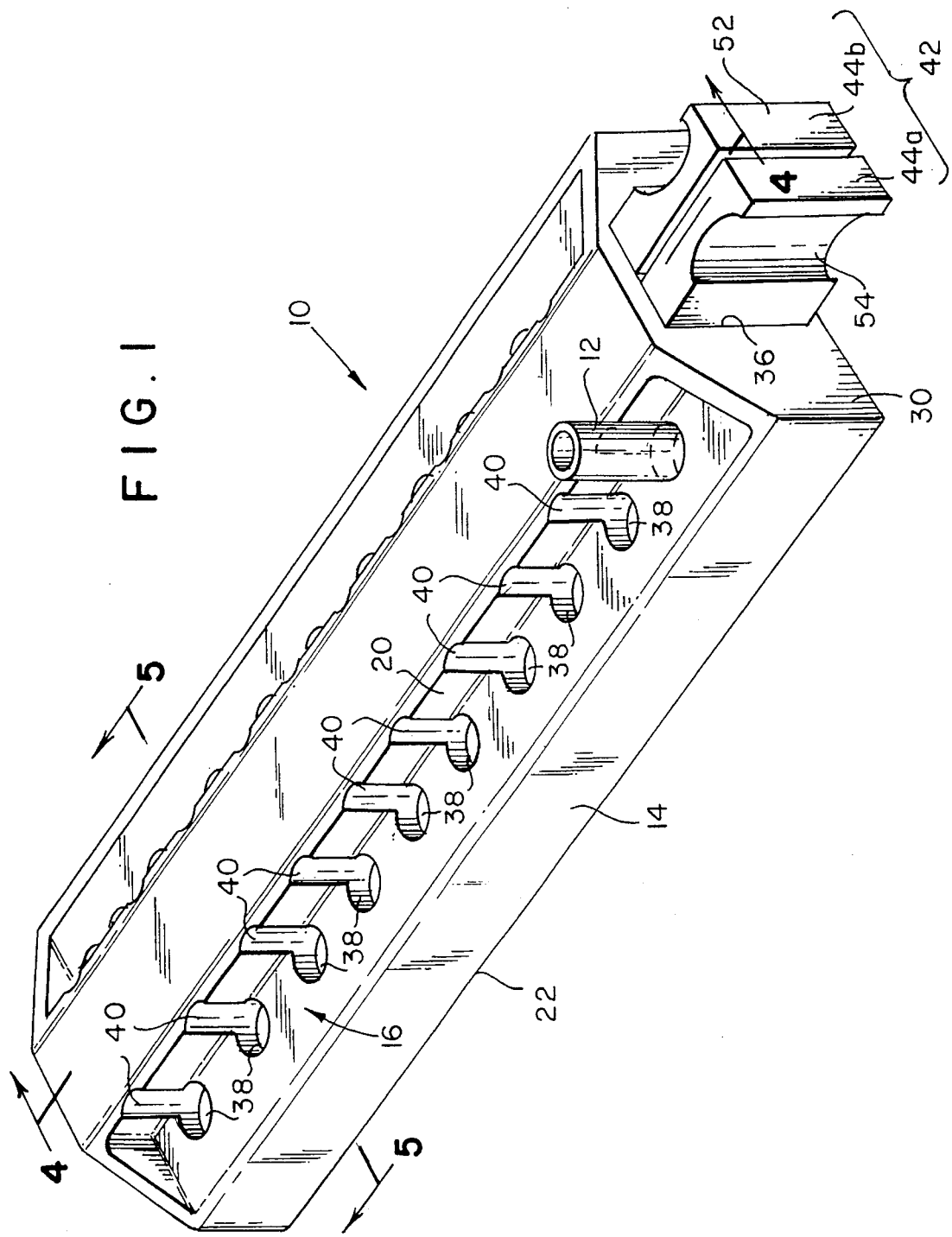
FIG. 1 is a perspective view of a magnetic capture rack according to the present invention.

Referring in general to FIGS. 1 through 5, there is shown a magnetic capture rack 10 according to the present invention. The rack 10 includes a substantially longitudinal housing portion 14, with a stepped upper surface 16, and a base or bottom surface 22. The stepped upper surface 16 includes a horizontal planar surface 18 and a vertical wall 20 joining with the horizontal planar surface. A plurality of wells or recesses 38 are formed in the horizontal planar surface 16. Each of the wells 38 receives a single test tube 12 therein in which a fluid suspension is contained for testing. Only a single test tube 12 is shown in FIG. 1 for simplicity, it being understood that the plurality of wells 38 could be filled to capacity in accordance with testing needs. The magnetic capture rack operates identically regardless of the number of wells actually containing a test tube. A plurality of vertical recesses 40 are formed in the vertical walls 20, the vertical recesses 40 corresponding in a one-to one alignment with the plurality of wells 38.

As best shown in FIG. 1, the plurality of wells are preferably positioned immediately adjacent the vertical wall 20 such that the plurality of recesses 40 formed in the vertical wall 20 become a part of a respective well 38. This arrangement assists in the stable positioning of the test tube or vial positioned within the well 38. Specifically, a base end of the test tube 12 will sit within the well 38, while a vertical wall of the test tube will rest against the vertical wall 20 of the stepped portion 16 of the housing 14. Additionally, with a well 38/recess 40 combination, the well portion can be more shallow than conventional test tube supports, since the recess 40 assists in positioning and stabilizing the test tube. A more shallow well also facilitates viewing the contents of the test tube 12. The number of wells is suited to the size of the housing 14 so that adjacent wells 38 do not come into contact with each other. Further, the size of the longitudinal bore 34 is intended to be sized to accommodate a slidable magnetic member 42 having sufficient strength to draw magnetic particles to be tested out of suspension.

Figure 3:
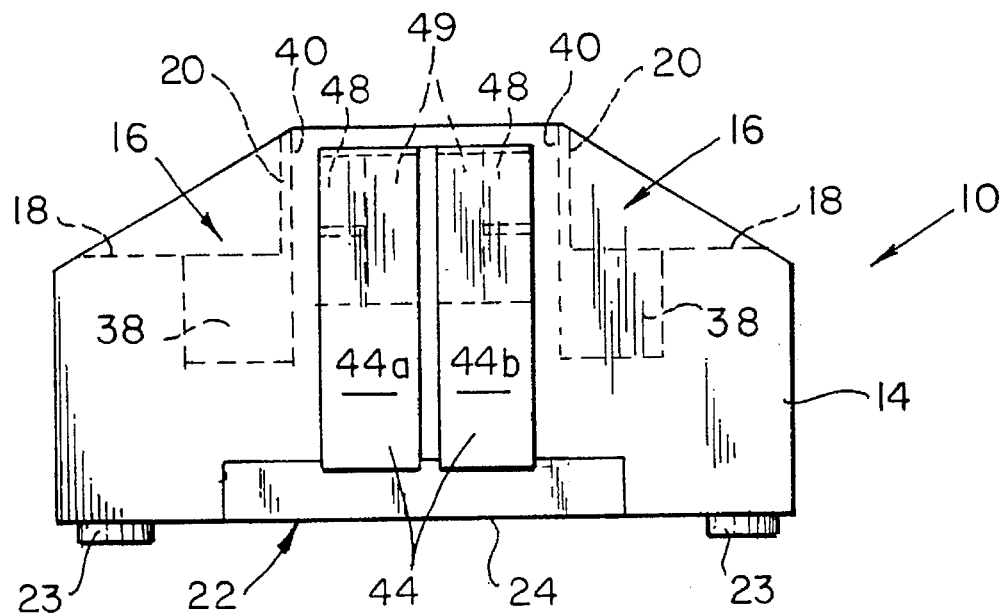
FIG. 3 is an end view of the rack shown in FIG. 1.
Figure 5:
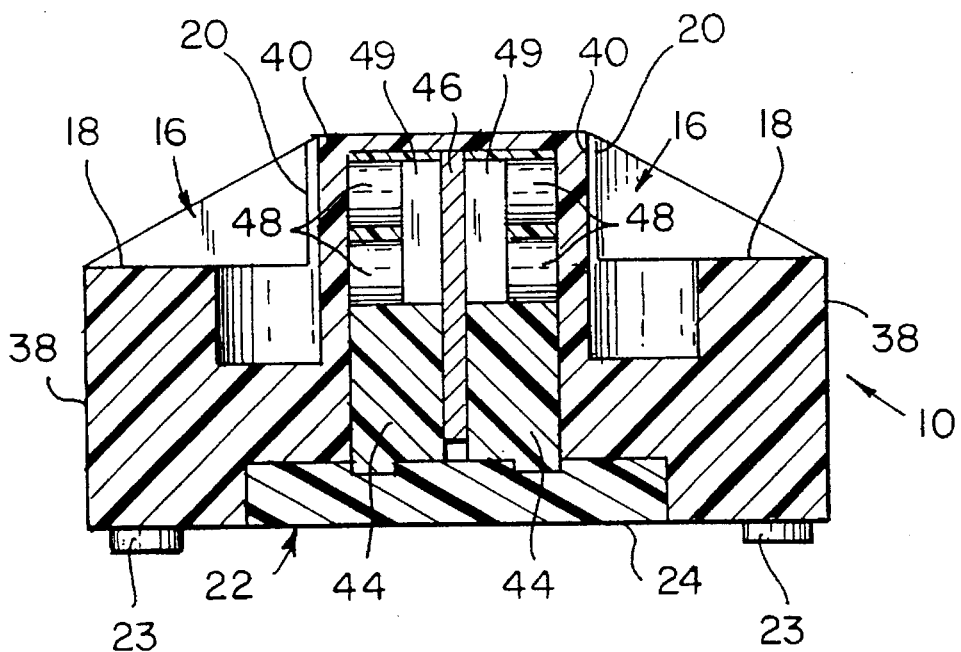
FIG. 5 is a cross-sectional view taken along lines 5—5 of FIG. 1.

The base 22 functions as the bottom support surface of the magnetic capture rack 10 and includes a sufficient number of support feet 23 thereon to prevent slippage or movement of the rack during use. Preferably, there are four support feet or foot pads of a resilient, non-skid material fixed by any suitable means to the base 22. Also provided in connection with the base 22 is a removable plate 24 as best shown in FIGS. 3 and 5. The removable plate 24 is positioned to be longitudinally aligned with a longitudinal axis of the rack 10 and is secured to the base 22 by a plurality of screws 28 as shown in FIG. 4. The removable plate 24 is particularly provided to enable access to the interior of the housing 14 for reasons which will be more fully explained hereinbelow.

The longitudinal bore 34 is integrally formed within the housing 14 as shown in FIG. 4. It is intended that the longitudinal bore extend substantially the entire length of the housing 14. The housing 14 is constructed such that there is an opening 36 in a first end 30 of the housing 14 which is the opening of the longitudinal bore 34. A second end 32 of the housing is closed thereby defining an end of the longitudinal bore 34 and acting as a stopper to the slidable magnetic member 42. The longitudinal bore 34 is specifically constructed of a substantially elongated rectangular prism to receive therein the slidable magnetic member 42.

The slidable magnetic member 42 is formed of a pair of bars 44 of a non-magnetic material with a magnetic plate 46 sandwiched therebetween as shown in FIGS. 3 and 5. The pair of non-magnetic bars 44 and the magnetic plate 46 combine to form the slidable magnetic member 42 also shaped as a longitudinally oriented rectangular prism. A plurality of magnetic slugs 48 are formed within each of the pair of non-magnetic bars 44 at an outer surface thereof and oriented transverse to the longitudinal axis of the housing and hence non-magnetic members. The transverse magnetic slugs 48 are best shown in FIG. 4 and are substantially evenly spaced to correspond to each of the plurality of wells 38 formed in the stepped surface 16 of the housing 14. As shown, a vertically aligned pair of magnetic slugs 48 are provided for each of the plurality of wells 38 and are in both of the pair of non-magnetic bars. An innermost end of each of the plurality of magnetic slugs 48 abuts against a yoke member 49 which in turn abuts against the longitudinally oriented magnetic plate 46 sandwiched between the pair of non-magnetic bars 44. The plurality of magnetic slugs 48 are arranged to be magnetically attracted to the yoke 49 and the yoke 49 is arranged to be magnetically attracted to the longitudinal magnetic plate 46, thereby increasing the magnetic draw against magnetic particles in suspension within a test tube 12.

A first end 56 of the slidable magnetic member 42 includes a gripping portion 52. The gripping portion 52 is formed of a flat mating side corresponding to the sides of the pair of non-magnetic bars 44 facing the magnetic plate 46 and a gripping surface having a recess 54 formed in an outer face of each of the non-magnetic bars 44 as shown in FIG. 1. The pair of non-magnetic bars 44 are secured together with the magnetic plate 46 by a plurality of screws 50 such that the slidable magnetic member 42 is of an integral construction. A second end 58 of the slidable magnetic member 42 is flat to abut against an inner end of the second end 32 of the longitudinal bore 34. The closed inner end of the longitudinal bore thus acts as a stopper for limiting the sliding movement of the slidable magnetic member 42.

The second end of the slidable magnetic member 42 also includes a depending stopper member 60 formed in the ends of the pair of non-magnetic bars 44. Upon sliding of the magnetic member 42 to an extended position out of the longitudinal bore 34, the magnetic member 42 is prevented from complete removal from the housing by the stopper member 60 engaging with a lip 26 projecting from an inner base floor of the longitudinal bore 34 at the first end 30 of the housing 14. Thus, bidirectional movement of the slidable magnetic member 42 can be controlled or "stopped" in either direction upon insertion or removal thereof from the housing 14.

It should be further understood that the extension of the slidable magnetic member 42 to an exterior of the housing 14 is such that complete extension thereof will completely separate all magnetic surfaces and all magnetic attraction from alignment with the wells 38 and any test tubes seated within the wells 38. This enables the selective attraction of any magnetic particles in a solution within the test tube 12 to be tested repeatedly, if necessary, without physically removing the test tube from the well 38 and without the need to disassemble the magnetic rack 10.

As indicated previously, the removable portion 24 of the base 22 enables access to the interior of the housing 14. In particular, separation of the removable base portion 24 from the base 22 will facilitate access to the longitudinal bore 34 and slidable magnetic member 42 for assembly and maintenance thereof.

The non-magnetic materials of the present invention are preferably formed of a heavy plastic or ceramic that will not interfere with the magnetic properties of the slidable magnetic member 42 and which will also enable screw type attachment of parts together. Additionally, the material of the housing member 14 may be either clear to further facilitate viewing of the contents of the test tube 12 or opaque if viewing of the contents is not necessary.

The magnetic rack 10 of the present invention therefore solves many of the construction problems and difficulty of operation encountered by those magnetic racks previously known. The reduced number of parts and the simplicity of construction offer lower manufacturing costs and less possibility of breakage and/or maintenance. Further, testing procedures are stabilized since there is no need to remove test tube vials from the rack to release particles into suspension and movement of the slidable magnetic member does not vibrate or interfere with the test tubes or solution therein.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A magnetic capture rack for holding a plurality of tubes, said rack comprising:

a primary housing member having an upper surface, a substantially planar base surface, and a single longitudinal bore formed in said primary housing, the upper surface having a longitudinally raised portion corresponding to said longitudinal bore and a recessed portion adjacent and longitudinally formed along each opposing side of said longitudinally raised portion, thereby defining a stepped upper surface, wherein said longitudinal bore is open at least at one end thereof;

a plurality of linearly arranged wells formed in the recessed portion of the upper surface of said housing on at least one of the opposing sides of said longitudinal bore and along a length of said primary housing; and a slidable magnetic member conforming in outer surface shape to an inner surface shape of said longitudinal bore, said magnetic member being selectively slidable into and out of said longitudinal bore, while maintaining said plurality of linearly arranged wells in a stationary position.

2. The magnetic capture rack according to claim 1, wherein said plurality of linearly arranged wells are evenly spaced wells formed in said housing.

3. The magnetic capture rack according to claim 1, wherein said linearly arranged wells are formed as a single row along one of the opposing sides of said longitudinal bore within said primary housing member.

4. The magnetic capture rack according to claim 1, wherein said slidable magnetic member is substantially equal in length to said primary housing member.

5. The magnetic capture rack according to claim 1, wherein said slidable magnetic member is bidirectionally and manually movable in said longitudinal bore.

6. The magnetic capture rack according to claim 1, wherein said slidable magnetic member includes an elongated magnetic bar.

7. The magnetic capture rack according to claim 1, wherein an end of said slidable magnetic bar includes a gripping portion positioned at an exterior of said primary housing member.

8. The magnetic capture rack according to claim 1, wherein said plurality of linearly arranged wells formed in the recessed portion of the upper surface of said housing are formed along both opposing sides of the longitudinal bore and along an entire length of said primary housing.

9. The magnetic capture rack according to claim 1, wherein said slidable magnetic member includes a pair of elongated non-magnetic bars and an elongated magnetic plate sandwiched between the pair of elongated non-magnetic bars.

10. The magnetic capture rack according to claim 9, further comprising means for securing the pair of elongated non-magnetic bars and elongated magnetic plate together in alignment.

11. A magnetic capture rack for holding a plurality of tubes, said rack comprising:

a primary housing member having a stepped upper surface, a substantially planar base surface, and a longitudinal bore formed in said primary housing, said stepped upper surface being defined by a longitudinally raised portion corresponding to said longitudinal bore and a recessed portion adjacent each opposing side of said longitudinally raised portion;

means for supporting said plurality of tubes within said primary housing, said means for supporting being formed in the recessed portion of said stepped upper surface of said primary housing at a predetermined depth and adjacent at least one of the opposing sides of said longitudinal bore; and a slidable magnetic member conforming in outer surface shape to an inner surface shape of said longitudinal bore, said magnetic member being selectively slidable into and out of said longitudinal bore and adjacent said means for supporting;

wherein a sliding insertion of said magnetic member within said longitudinal bore attracts magnetic particles in suspension within said plurality of tubes toward said magnetic member and wherein a sliding removal of said magnetic member from said longitudinal bore releases the magnetic particles into suspension within said plurality of tubes.

12. The magnetic capture rack according to claim 11, wherein said means for supporting includes a plurality of evenly spaced wells formed in said housing.

13. The magnetic capture rack according to claim 11, wherein said means for supporting includes at least one recess formed in said housing member and adjacent said longitudinal bore.

14. The magnetic capture rack according to claim 11, wherein said wells are formed as at least one single row with each single row being formed along opposite sides of said longitudinal bore within said primary housing member.

15. The magnetic capture rack according to claim 11, wherein said slidable magnetic member is substantially equal in length to said primary housing member.

16. The magnetic capture rack according to claim 11, wherein said slidable magnetic member is bidirectionally and manually movable in said longitudinal bore.

17. The magnetic capture rack according to claim 11, wherein an end of said slidable magnetic bar includes a gripping portion continually exposed to an exterior of said primary housing member.

18. The magnetic capture rack according to claim 11, wherein said slidable magnetic member includes a pair of elongated non-magnetic bars and an elongated magnetic plate sandwiched between the pair of elongated non-magnetic bars.

19. The magnetic capture rack according to claim 18, further comprising means for securing the pair of elongated non-magnetic bars and elongated magnetic plate together in alignment.

20. The magnetic capture rack according to claim 18, further comprising a plurality of evenly spaced slugs formed at an upper surface of each of the pair of elongated non-magnetic bars and a yoke linearly positioned between the slugs and the elongated magnetic plate.

21. A magnetic capture rack for holding a plurality of tubes, said rack comprising:

a primary housing member having an upper surface, a substantially planar base surface, and a single longitudinal bore formed in said primary housing, the upper surface having a longitudinally raised portion corresponding to said longitudinal bore and a recessed portion adjacent and longitudinally formed along each opposing side of said longitudinal bore, thereby defining a stepped upper surface, wherein said longitudinal bore is open at least at one end thereof;

a plurality of linearly arranged wells integrally formed in the recessed portion of the upper surface of said housing on at least one of the opposing sides of said longitudinal bore and along a length of said primary housing; and a slidable magnetic member conforming in outer surface shape to an inner surface shape of said longitudinal bore, said slidable magnetic member including a pair of elongated non-magnetic bars and an elongated magnetic plate sandwiched between the pair of elongated non-magnetic bars, a plurality of evenly spaced slugs formed at an upper surface of each of the pair of elongated non-magnetic bars, and a yoke linearly positioned between the slugs and the elongated magnetic plate, wherein said magnetic member is selectively slidable into and out of said longitudinal bore while maintaining said plurality of linearly arranged wells in a stationary position.

22. The magnetic capture rack according to claim 21, wherein said plurality of linearly arranged wells are evenly spaced wells formed in said housing.

23. The magnetic capture rack according to claim 21, wherein said linearly arranged wells are formed as a single row along one of the opposing sides of said longitudinal bore within said primary housing member.

24. The magnetic capture rack according to claim 21, wherein said slidable magnetic member is substantially equal in length to said primary housing member.

25. The magnetic capture rack according to claim 21, wherein said slidable magnetic member is bidirectionally and manually movable in said longitudinal bore.

26. The magnetic capture rack according to claim 21, further comprising means for securing the pair of elongated non-magnetic bars and elongated magnetic plate together in alignment.

27. The magnetic capture rack according to claim 21, wherein an end of said slidable magnetic member includes a gripping portion positioned at an exterior of said primary housing member.

28. The magnetic capture rack according to claim 21, wherein said plurality of linearly arranged wells formed in the recessed portion of the upper surface of said housing are formed along both opposing sides of the longitudinal bore and along an entire length of said primary housing.

* * * * *